(12) United States Patent
Solomon

(10) Patent No.: US 11,518,947 B2
(45) Date of Patent: Dec. 6, 2022

(54) DISPERSION OF HEXAMINE IN NON-AQUEOUS GLYCERINE

(71) Applicant: Ecolab USA Inc., St. Paul, MN (US)

(72) Inventor: Kim R. Solomon, River Falls, WI (US)

(73) Assignee: ECOLAB USA Inc., St. Paul, MN (US)

(*) Notice: Subject to any disclaimer, the term of this patent is extended or adjusted under 35 U.S.C. 154(b) by 80 days.

(21) Appl. No.: 15/935,569

(22) Filed: Mar. 26, 2018

(65) Prior Publication Data

US 2018/0282636 A1 Oct. 4, 2018

Related U.S. Application Data

(60) Provisional application No. 62/478,429, filed on Mar. 29, 2017.

(51) Int. Cl.
| | | |
|---|---|---|
| *C10G 29/20* | (2006.01) | |
| *C10G 29/22* | (2006.01) | |
| *C10C 3/02* | (2006.01) | |
| *C07D 487/18* | (2006.01) | |

(52) U.S. Cl.
CPC ........... *C10G 29/20* (2013.01); *C07D 487/18* (2013.01); *C10C 3/026* (2013.01); *C10G 29/22* (2013.01); *C10G 2300/207* (2013.01)

(58) Field of Classification Search
CPC .. C10G 29/20; C10G 29/22; C10G 2300/207; C04B 26/26; C04B 41/5315; C04B 2111/00017; C10C 3/026; C07D 487/18; C08K 5/3477; C08L 95/00; C02F 2101/101
See application file for complete search history.

(56) References Cited

U.S. PATENT DOCUMENTS

| | | | |
|---|---|---|---|
| 5,213,680 A * | 5/1993 | Kremer | ................. C10G 29/20 208/189 |
| 6,444,117 B1 | 9/2002 | Khan et al. | |
| 7,264,786 B2 | 9/2007 | Pakulski et al. | |
| 9,409,119 B2 | 8/2016 | Murai et al. | |
| 2005/0130847 A1 | 6/2005 | Gatlin et al. | |
| 2016/0009980 A1 | 1/2016 | Gupta et al. | |
| 2017/0022109 A1 * | 1/2017 | Poland | ................... C08K 5/521 |
| 2018/0105729 A1 * | 4/2018 | Hamilton | ............... C09K 8/532 |

FOREIGN PATENT DOCUMENTS

| | | |
|---|---|---|
| CN | 101889568 A | 11/2010 |
| CN | 102140364 A | 3/2011 |
| CN | 104327588 A | 2/2015 |
| RU | 2230096 C1 | 6/2004 |
| RU | 2269567 C1 | 2/2006 |
| RU | 2302523 | 7/2007 |
| RU | 2479615 | 4/2013 |
| RU | 2522459 C1 | 7/2014 |
| RU | 2577556 C1 | 3/2016 |
| UA | 85923 | 12/2013 |
| WO | WO 9301126 | 1/1993 |

OTHER PUBLICATIONS

Forno, C., "The Growth of Large Crystals of Hexamine From Solution" Journal of Crystal Growth (1974) 21: 61-64.

* cited by examiner

*Primary Examiner* — Prem C Singh
*Assistant Examiner* — Brandi M Doyle
(74) *Attorney, Agent, or Firm* — Eric D. Babych; Barnes & Thorburg LLP

(57) ABSTRACT

The present disclosure generally relates to dispersions useful for scavenging hydrogen sulfide. The dispersions may be anhydrous and contain a solvent and a hydrogen sulfide scavenging compound. The hydrogen sulfide scavenging compound may be hexamine, for example. The solvent may be a $C_{2-8}$ polyol, such as glycerin.

7 Claims, No Drawings

DISPERSION OF HEXAMINE IN NON-AQUEOUS GLYCERINE

BACKGROUND

1. Field of the Invention

The present disclosure generally relates to hydrogen sulfide scavengers. More particularly, the disclosure pertains to the use of dispersions of hexamine to scavenge hydrogen sulfide.

2. Description of the Related Art

Petroleum asphalt is produced as a residue of a thermal separation refinery process. The thermal separation process causes thermal cracking to occur, which frequently causes hydrogen sulfide to be present in the asphalt stream. In fact, thermal cracking continues in the asphalt even after the asphalt has left the vacuum distillation section of the operation, particularly at high temperature. In order to permit safe loading, handling, and storage of the asphalt, it is necessary to reduce the hydrogen sulfide to safe levels in the asphalt. Prior art methods of reducing hydrogen sulfide not only take a considerable amount of time (several days), but some methods release hydrogen sulfide into the vapor space during storage, which could create hazardous conditions. Moreover, environmental regulations around the globe stress the limits on the hydrogen sulfide content of vent gas.

BRIEF SUMMARY

The present disclosure provides dispersions useful for scavenging hydrogen sulfide. In some embodiments, a dispersion is disclosed, which comprises a $C_2$-$C_8$ polyol and a compound of formula (I) or formula (II):

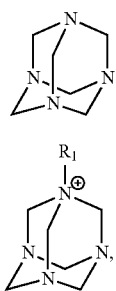

wherein $R_1$ is a substituted or unsubstituted $C_{1-32}$ alkyl, a substituted or unsubstituted $C_{2-32}$ alkenyl, or a substituted or unsubstituted $C_{2-32}$ alkynyl, and wherein the substituted $C_{1-32}$ alkyl, the substituted $C_{2-32}$ alkenyl, and the substituted $C_{2-32}$ alkynyl are substituted with a hydroxyl or a $C_{1-5}$ alkyl.

In some embodiments, the dispersion excludes a monolignol alcohol. The $C_{2-8}$ polyol may be glycerin. In certain embodiments, the dispersion comprises about 1% or less, by weight, of water. In other embodiments, the dispersion excludes water.

In some embodiments, the dispersion comprises at least about 35% by weight of the compound of formula (I) or formula (II). In certain embodiments, the dispersion comprises about 65% or less, by weight, of the $C_2$-$C_8$ polyol. The dispersion may comprise a pH greater than about 7.

In some embodiments, the $C_2$-$C_8$ polyol comprises a boiling point selected from the group consisting of greater than about 150° C., greater than about 200° C., and greater than about 240° C. In certain embodiments, the compound of formula (I) is hexamine.

In other embodiments, the present disclosure provides methods for scavenging hydrogen sulfide. A method may comprise adding an effective amount of a dispersion to a medium, wherein the dispersion comprises a $C_2$-$C_8$ polyol and a compound of formula (I) or formula (II):

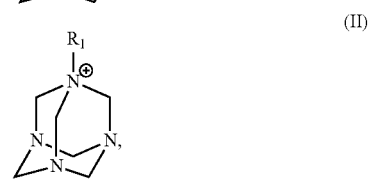

wherein $R_1$ is a substituted or unsubstituted $C_{1-32}$ alkyl, a substituted or unsubstituted $C_{2-32}$ alkenyl, or a substituted or unsubstituted $C_{2-32}$ alkynyl, and wherein the substituted $C_{1-32}$ alkyl, the substituted $C_{2-32}$ alkenyl, and the substituted $C_{2-32}$ alkynyl are substituted with a hydroxyl or a $C_{1-5}$ alkyl.

In some embodiments, the medium comprises a member selected from the group consisting of crude oil, diesel fuel, asphalt, and any combination thereof. In certain embodiments, the medium comprises polyphosphoric acid. The effective amount may be from about 1 ppm to about 5,000 ppm.

In still further embodiments, the present disclosure provides a solution comprising, consisting of, and/or consisting essentially of a compound of formula (I) and/or a compound of formula (II) and a $C_2$-$C_8$ polyol, such as glycerin. The solution may be used in any of the methods of scavenging hydrogen sulfide disclosed herein. The solution may be used in addition to one or more of the dispersions disclosed herein or the solution may be used instead of a dispersion in any of the methods of scavenging hydrogen sulfide disclosed herein.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

DETAILED DESCRIPTION

Various embodiments are described below. The relationship and functioning of the various elements of the embodiments may better be understood by reference to the following detailed description. However, embodiments are not limited to those explicitly described below. In certain instances, details may have been omitted that are not necessary for an understanding of embodiments disclosed herein.

Environmental and safety standards require the removal of hydrogen sulfide from oil, asphalt, and/or other materials. In some instances, hexamine may be used as a hydrogen sulfide scavenger. Hexamine decomposes, in the presence of acid, to ammonia and formaldehyde. Formaldehyde and/or ammonia can then react with hydrogen sulfide, converting the volatile and toxic gas into a nonvolatile material. For example, the formaldehyde can react with hydrogen sulfide to form triathane. Despite the usefulness of hexamine, it has limited solubility in common solvents. Some solvents that can effectively dissolve hexamine are volatile and incompatible with compositions that need to be added to hot asphalt.

Hexamine is commercially available in a hexahydrate form, which melts at about 13° C. This is commonly referred to as an "aqueous solution" of hexamine. Hexamine is also commercially available in an anhydrous, solid form with a melting point of about 280° C. Hexamine has limited solubility in common organic solvents at 20° C. Exemplary solubility values include: 13.4 g in chloroform, 7.25 g in methanol, 2.89 g in ethanol, 0.65 g in acetone, 0.23 g in benzene, 0.14 g in xylene, 0.06 g in ether, and about 0 g in petroleum ether. Chloroform is not suitable due to toxicity, and ethanol and acetone are too volatile for use in use in hot asphalt, which can be up to about 300 to 400° F.

Dispersions of the present disclosure are capable of completely removing (or at least reducing the amount of) hydrogen sulfide from mediums, such as crude asphalt, but do not suffer from the same solubility issues associated with hexamine solutions. In some embodiments, the dispersions do not interfere with any polyphosphoric acid that may be present in the material containing the hydrogen sulfide. The dispersions may be non-aqueous and non-volatile, which is ideal for applications involving hot materials, such as asphalt. The dispersions may be halogen-free, which is desirable for improved worker safety.

In some embodiments, dispersions are disclosed for scavenging hydrogen sulfide. The dispersions may include a hydrogen sulfide scavenger. The dispersions may be in the form of stable, non-aqueous suspensions of the hydrogen sulfide scavenger in a solvent. In some embodiments, the solvent is glycerin.

In some embodiments, the hydrogen sulfide scavenger may comprise formula (I) or formula (II):

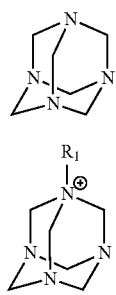

where $R_1$ may be a substituted or unsubstituted $C_{1-32}$ alkyl, a substituted or unsubstituted $C_{2-32}$ alkenyl, or a substituted or unsubstituted $C_{2-32}$ alkynyl. The substituted $C_{1-32}$ alkyl, substituted $C_{2-32}$ alkenyl, and substituted $C_{2-32}$ alkynyl may be substituted with a hydroxyl group or a $C_{1-5}$ alkyl.

In certain embodiments, $R_1$ may be a substituted or unsubstituted $C_{1-8}$ alkyl, a substituted or unsubstituted $C_{2-8}$ alkenyl, or a substituted or unsubstituted $C_{2-8}$ alkynyl. The substituted $C_{1-8}$ alkyl, substituted $C_{2-8}$ alkenyl, and substituted $C_{2-8}$ alkynyl may be substituted with a hydroxyl group or a $C_{1-5}$ alkyl.

The term "alkyl," as used herein, refers to a linear or branched hydrocarbon, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons). Illustrative, non-limiting examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term "alkenyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbon atoms, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl.

The term "alkynyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbon atoms, and having one or more carbon-carbon triple bonds. Alkynyl groups include, but are not limited to, ethynyl, propynyl, and butynyl.

In some embodiments, the compound of formula (I) may be hexamine, which is also known as hexamethylenetetramine, methenamine, urotropine, 1,3,5,7-tetraazaadamantane, formin, aminoform, or 1,3,5,7-tetraazatricyclo [3.3.1.1$^{3,7}$]decane. Hexamine is readily available from various chemical suppliers.

The dispersions disclosed herein exclude (do not comprise) a monolignol alcohol. For example, in some embodiments, the dispersions may consist of a hydrogen sulfide scavenger, such as hexamine, and a solvent, such as glycerin. In other embodiments, the dispersions may consist of a hydrogen sulfide scavenger, a solvent, and less than about 1%, by weight, of water.

In certain embodiments, the dispersions comprise at least about 35%, by weight, of a hydrogen sulfide scavenger, such as a compound comprising formula (I) and/or formula (II). For example, the dispersions may comprise at least about 35%, by weight, of a compound of formula (I) and/or formula (II), at least about 40%, by weight, of a compound of formula (I) and/or formula (II), or at least about 55%, by weight, of a compound of formula (I) and/or formula (II). The amount of the compound of formula (I) and/or formula (II) in the dispersion is not particularly limited and, in some embodiments, may be at least about 70%, at least about 80%, or at least about 90%, by weight, of a compound of formula (I) and/or formula (II). In certain embodiments, the amount of the compound of formula (I) and/or formula (II) may be selected based upon the desired application of the dispersion and/or the estimated amount of hydrogen sulfide in the medium.

Various solvents may be included in the dispersions. The dispersions may include a single solvent or they may include any combination of solvents. In some embodiments, the solvent comprises a $C_{2-8}$ polyol. A polyol may be defined as an alcohol having multiple hydroxyl groups. In some embodiments, the composition may include a $C_{3-8}$ polyol, a $C_{4-8}$ polyol, or a $C_{5-8}$ polyol. In certain embodiments, the $C_{2-8}$ polyol is glycerin.

Glycerin is hydroscopic and may contain water. Water content in commercially available glycerin can be as low as about 1%, by weight, or less. In some embodiments, the dispersions may include an amount of water that is less than about 1% by weight. The glycerin may be prepared such that all of the water is removed, such as by using molecular sieves. In certain embodiments, a dispersion may exclude (or not comprise) water.

In some embodiments, the dispersion may comprise from about 2 to about 65 weight percent of the solvent. For example, the dispersion may comprise about 65 weight percent or less of the solvent, about 60 weight percent or less of the solvent, or about 45 weight percent or less of the solvent. The dispersion may comprise from about 2 to about 60 weight percent of the solvent, from about 2 to about 45 weight percent of the solvent, from about 2 to about 40 weight percent, from about 2 to about 30 weight percent of the solvent, or from about 2 to about 25 weight percent of the solvent.

Depending upon the desired application, the amounts of the hydrogen sulfide scavenger and the solvent can vary according to the guidelines set forth herein. For example, a dispersion may comprise about 60 weight % hexamine and about 40 weight % glycerin, about 52 weight % hexamine and about 48 weight % glycerin, or about 33 weight % hexamine and about 67 weight % glycerin. Other solvents/ scavengers may be included as well such that in certain embodiments, a dispersion may comprise more than one solvent and/or more than one hydrogen sulfide scavenger.

In some embodiments, the solvent has a boiling point of at least about 150° C. For example, the solvent may have a boiling point of at least about 175° C., at least about 200° C., at least about 240° C., etc. In general, when referring to a "stable" dispersion, the present disclosure contemplates a dispersion that is stable at about 20° C.

In some embodiments, the dispersion may have a pH greater than about 7. The dispersion may have a pH of about 7 to about 9, for example. Generally, it may be desirable to maintain the pH at neutral or alkaline conditions before adding the dispersion to the asphalt to avoid acid hydrolysis of hexamine.

In some embodiments, methods are provided where the dispersion(s) described herein may be added to a medium in an industrial process to scavenge hydrogen sulfide from the medium. Scavenging hydrogen sulfide includes, for example, reducing the level of hydrogen sulfide present in the medium and/or completely eliminating the hydrogen sulfide from the medium. The industrial process may utilize or process crude oil, diesel fuel, asphalt, and the like. The dispersion may be added to the medium, which may comprise crude oil, diesel fuel, asphalt, any combination thereof, and/or any other medium/material that contains hydrogen sulfide.

For example, the dispersion may be added to sour crude oil to scavenge hydrogen sulfide. In another embodiment, the dispersions of the present disclosure may be used to prepare solutions of hexamine-derived preservatives for use in industrial processes.

The dispersion may be added to the process continuously, dosed intermittently, or any combination thereof. A programmed logic controller (PLC) may control the addition of the dispersion to the industrial process. An industrial process may include sensors that detect levels of hydrogen sulfide and the sensors may send those levels to the PLC. The communication between the sensors and the PLC may be wired or wireless, for example. Communication protocols are well-known in the art. Once levels of hydrogen sulfide approach and/or reach a predetermined threshold, which may be programmed into the PLC, the dispersion may be added to the process in an amount sufficient to scavenge the hydrogen sulfide. In some embodiments, the amount of dispersion added is calculated based upon the amount of hydrogen sulfide detected in the system.

The dispersions disclosed herein may be added to the medium in an amount that can effectively scavenge hydrogen sulfide. The effective amount may depend upon, for example, the desired application and/or the amount of hydrogen sulfide in the medium. In some embodiments, the effective amount may be about 1 ppm or more. In other embodiments, the effective amount may be about 10 ppm or more, about 100 ppm or more, about 200 ppm or more, or from about 200 ppm to about 5,000 ppm, for example.

The dispersions and methods disclosed herein may be especially useful for scavenging hydrogen sulfide from hot asphalt/crude asphalt where the use of aqueous or volatile solvents presents safety or toxicity concerns. The dispersions provide a means for delivering a concentrated, nonvolatile, liquid form of hexamine. The present disclosure provides stable, liquid dispersions of solid hexamine particles suspended in a nonvolatile liquid.

EXAMPLES

In a first experiment, a slurry of about 2 g of hexamine in about 8 g of glycerin was prepared. The composition was allowed to sit undisturbed for about 48 hours and then the clear supernate was decanted off from the precipitated hexamine. NMR analysis of the supernate showed that the clear solution contained only 8% hexamine.

In a second experiment, a series of dispersions of hexamine in anhydrous glycerin were prepared. Each dispersion contained less than about 1%, by weight, of water. The dispersions were evaluated for settling for about 2 hours at about 20° C. and also at about 50° C. As the results in Table 1 illustrate, a dispersion of hexamine in glycerin afforded a stable suspension of a significantly higher concentration of hexamine solid particulate than did a solution of hexamine.

TABLE 1

|  | Wt. % Hexamine | Wt. % Glycerin | 20° C. Stability | 50° C. Stability |
| --- | --- | --- | --- | --- |
| Sample 1 | 33 | 67 | Slight separation | Separated |
| Sample 2 | 55 | 45 | Stable | Very slight separation |
| Sample 3 | 67 | 33 | Stable | Stable |

In certain cases, dispersions were prepared by pre-heating glycerin to about 150° F. in an oven, removing the pre-heated sample from the oven, and then mixing in the scavenger, which was hexamine, until the samples were cloudy/opaque but no discrete particles could be observed by the naked eye. The samples were then placed back into the oven at about 150° F. for about 2 hours.

A sample comprising about 60 weight % hexamine and about 40 weight % glycerin showed no separation in the oven but it was quite viscous at room temperature. A sample comprising about 52 weight % hexamine and about 48 weight % glycerin and a sample comprising about 33 weight % hexamine and about 67 weight % glycerin showed slight separation in the oven but looked much easier to handle at room temperature than the sample comprising 60 weight % hexamine.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a compound" is intended to include "at least one compound" or "one or more compounds."

Any composition disclosed herein may comprise, consist of, or consist essentially of any of the compounds/components disclosed herein. In accordance with the present disclosure, the phrases "consist essentially of," "consists essentially of," "consisting essentially of," and the like, limit the scope of a claim to the specified materials or steps and those materials or steps that do not materially affect the basic and novel characteristic(s) of the claimed invention.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method of scavenging hydrogen sulfide from a medium in an industrial process, comprising:
adding an effective amount of a dispersion to the medium, wherein the dispersion comprises a $C_2$-$C_5$ polyol and a compound of formula (I) or formula (II):

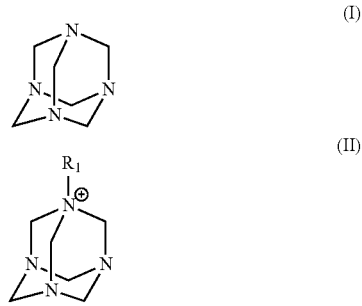

wherein $R_1$ is a substituted or unsubstituted $C_{1-32}$ alkyl, a substituted or unsubstituted $C_{2-32}$ alkenyl, or a substituted or unsubstituted $C_{2-32}$ alkynyl, and wherein the substituted $C_{1-32}$ alkyl, the substituted $C_{2-32}$ alkenyl, and the substituted $C_{2-32}$ alkynyl are substituted with a hydroxyl or a $C_{1-5}$ alkyl, wherein the dispersion comprises at least about 67% by weight of the compound of formula (I) or formula (II), wherein the dispersion is prepared by pre-heating the $C_2$-$C_5$ polyol to about 150° F. and then adding the compound of formula (I) or formula (II) to the $C_2$-$C_5$ polyol to form the dispersion.

2. The method of claim 1, wherein the medium comprises a member selected from the group consisting of crude oil, diesel fuel, asphalt, and any combination thereof.

3. The method of claim 1, wherein the medium comprises polyphosphoric acid.

4. The method of claim 1, wherein the effective amount is from about 1 ppm to about 5,000 ppm.

5. The method of claim 1, wherein the dispersion comprises a pH greater than about 7.

6. A method of scavenging hydrogen sulfide from a medium in an industrial process, comprising:
adding an effective amount of a dispersion to the medium, wherein the dispersion comprises glycerin and at least about 67% by weight of hexamine, further wherein the dispersion is prepared by pre-heating the glycerin to about 150° F. and then adding the hexamine to the glycerin to form the dispersion.

7. The method of claim 6, wherein the medium is asphalt.

* * * * *